United States Patent [19]

Williams, III et al.

[11] 4,455,431
[45] Jun. 19, 1984

[54] METHOD FOR MAKING BIS-ETHERPHTHALIMIDES

[75] Inventors: Frank J. Williams, III, Scotia, N.Y.; Brent A. Dellacoletta, Evansville, Ind.

[73] Assignee: General Electric Company, Schenectady, N.Y.

[21] Appl. No.: 354,978

[22] Filed: Mar. 5, 1982

[51] Int. Cl.$^3$ .......................................... C07D 209/48
[52] U.S. Cl. ..................... 548/461; 548/474; 548/426
[58] Field of Search ............... 548/461, 476, 480; 568/722, 723, 724

[56] References Cited

U.S. PATENT DOCUMENTS

| | | | |
|---|---|---|---|
| 3,992,406 | 11/1976 | Markezich | 548/461 |
| 4,005,102 | 1/1977 | Cook et al. | 548/481 |
| 4,020,069 | 4/1977 | Johnson et al. | 548/461 |
| 4,086,081 | 4/1978 | Barrons et al. | 71/126 |
| 4,181,794 | 1/1980 | Kim et al. | 528/496 |
| 4,257,953 | 3/1981 | Williams et al. | 548/461 |
| 4,261,893 | 4/1981 | Boguslaski et al. | 548/480 |
| 4,273,712 | 6/1981 | Williams | 260/326 N |
| 4,302,616 | 11/1981 | Williams et al. | 568/722 |
| 4,374,974 | 2/1983 | Hay et al. | 529/219 |

FOREIGN PATENT DOCUMENTS 7408880  1/1976  Netherlands ................. 548/461

Primary Examiner—Donald G. Daus
Assistant Examiner—G. Hendricks
Attorney, Agent, or Firm—William A. Teoli; James C. Davis, Jr.; James Magee, Jr.

[57] ABSTRACT

A simplified method is provided for making aromatic bis-etherphthalimides by employing a polychlorinated $C_{(1-3)}$ alkane solution of nitro-N-organophthalimide directly with alkali metal bisphenoxide salt in a refluxing nonpolar organic solvent. After the polychlorinated $C_{(1-3)}$ alkane has completely distilled from the mixture, a phase transfer catalyst is added. As a result, the requirement for isolating and handling nitro-N-organophthalimide solids prior to condensation with alkali metal bisphenoxide salts is thereby eliminated.

10 Claims, No Drawings

METHOD FOR MAKING BIS-ETHERPHTHALIMIDES

BACKGROUND OF THE INVENTION

Prior to the present invention, as shown for example by Williams et al, U.S. Pat. No. 4,257,953, assigned to the same assignee as the present invention, aromatic bis-etherphthalimides were prepared by reacting bisphenoxide salts with nitro-substituted N-organophthalimides, for example, 4-nitro-N-methylphthalimide, or a mixture thereof with 3-nitro-N-methylphthalimide. These nitro-substituted N-organophthalimides can be made by the process as shown by Cook et al, U.S. Pat. No. 4,005,102, assigned to the same assignee as the present invention.

In Cook et al, the nitration of N-organophthalimides is achieved by refluxing a mixture of the N-organophthalimide, concentrated nitric acid, concentrated sulfuric acid and methylene chloride to produce the corresponding nitro-substituted N-organophthalimide. The desired nitrophthalimide is then initially isolated from the nitration mixture as the organic methylene chloride phase. The methylene chloride phase is then combined with the methylene chloride extract of the acid phase and the total passed through a column of silica gel to remove traces of sulfuric acid. The nitrophthalimide was then recovered by evaporation of the methylene chloride.

The aromatic bis-etherphthalimide was then made in accordance with the above Williams et al patent, which utilizes the nitrophthalimide in a heterogeneous mixture of the alkali metal bisphenoxide salt, nonpolar organic solvent and phase transfer catalyst. Although the aforementioned procedure involving the isolation of the nitrophthalimide from the nitration reaction mixture prior to its reaction with the bisphenoxide salt achieves valuable results, it nevertheless requires the time consuming step of isolating and handling the nitrophthalimide prior to its contact with the alkali metal bisphenoxide salt.

The present invention is based on the discovery that aromatic bis-etherphthalimides can be made without the isolation of the nitro-substituted N-organophthalimide from a polychlorinated $C_{(1-3)}$ alkane solution obtained from the nitration reaction mixture, by directly utilizing the polychlorinated $C_{(1-3)}$ alkane phase of the nitration reaction mixture consisting of a solution of the nitrophthalimide in the polychlorinated $C_{(1-3)}$ alkane with a mixture of alkali metal bisphenoxide salt and nonpolar solvent. Preferably, the addition of the polychlorinated $C_{(1-3)}$ alkane solution of the nitro-substituted N-organophthalimide to the alkali metal bisphenoxide salt is achieved while the bisphenoxide salt is in contact with the nonpolar organic solvent while it is refluxing. After the polychlorinated $C_{(1-3)}$ alkane has completely distilled from the resulting reaction mixture, the phase transfer catalyst can be added. Otherwise, undesirable side-reaction can occur resulting in undesirable polychlorinated $C_{(1-3)}$ alkane polymeric reaction products.

STATEMENT OF THE INVENTION

In the process for making bis-etherphthalimide involving the steps of,
(A) nitrating N-organophthalimide with concentrated nitric acid,
(B) isolating the resulting nitrophthalimide from the nitration mixture of (A) as a polychlorinated $C_{(1-3)}$ alkane solution,
(C) treating the polychlorinated $C_{(1-3)}$ alkane solution of (B), to remove traces of mineral acid,
(D) evaporating the polychlorinated $C_{(1-3)}$ from the solution of (C) to recover the nitro-N-organophthalimide,
(E) reacting the nitrophthalimide of (D) with an alkali metal bisphenoxide salt, the improvement which comprises,
(1) adding the nitration mixture of (C) directly to a mixture of alkali metal bisphenoxide salt and a nonpolar organic solvent while the latter is refluxing, in amounts sufficient to produce a reaction mixture having about two moles of nitrophthalimide, per mole of bisphenoxide salt, which refluxing mixture of bisphenoxide salt and nonpolar organic solvent is obtained by heating under azeotropic conditions, a mixture of bisphenoxide, water, alkali metal hydroxide, and said nonpolar organic solvent until the mixture is substantially anhydrous,
(2) distilling a major amount of the nonpolar organic solvent from the resulting mixture of (1), to provide for the complete removal of polychlorinated $C_{(1-3)}$ alkane used in the treated solution of (C),
(3) adding to the resulting mixture of (2) an effective amount of a phase transfer catalyst,
(4) refluxing the resulting mixture of (3),
(5) extracting the resulting mixture of (4) with aqueous alkali metal hydroxide and
(6) effecting the removal of nonpolar organic solvent from the organic phase resulting from the extraction step of (5), whereby the handling and isolation of the nitrophthalimide solids of (C), prior to the reaction of such solids with the alkali metal bisphenoxide salt of (E) is eliminated.

Included by the alkali metal salts of the diphenoxides which can be utilized in the practice of the present invention are sodium and potassium salts of the following dihydric phenols:

2,2-bis-(2-hydroxyphenyl)propane;
2,4'-dihydroxydiphenylmethane;
bis-(2-hydroxyphenyl)methane;
2,2-bis(4-hydroxyphenyl)propane, hereinafter identified as "bisphenol-A" or "BPA";
1,1-bis-(4-hydroxyphenyl)ethane;
1,1-bis-(4-hydroxyphenyl)propane;
2,2-bis-(4-hydroxyphenyl)pentane;
3,3-bis-(4-hydroxyphenyl)pentane;
4,4'-dihydroxybiphenyl;
4,4'-dihydroxy-3,3,5,5'-tetramethylbiphenyl;
2,4'-dihydroxybenzophenone;
4,4'-dihydroxydiphenylsulfone;
2,4'-dihydroxydiphenylsulfone;
4,4'-dihydroxydiphenyl sulfoxide;
4,4'-dihydroxydiphenyl sulfide;
hydroquinone;
resorcinol;
3,4'-dihydroxydiphenylmethane; and
4,4'-dihydroxydiphenylether.

Some of the nitro-N-organophthalimides which can be used in the practice of the present invention are, for example, 4-nitro-N-methylphthalimide, 4-nitro-N-ethylphthalimide, 3-nitro-N-methylphthalimide, a mixture of 4-nitro-N-methylphthalimide and 3-nitro-N-methylphthalimide, etc.

Included by the polychlorinated $C_{(1-3)}$ alkanes which can be used in the practice of the present invention are, for example, methylene chloride, trichloroethane and 1,2-dichloroethane.

Phase transfer catalysts which can be used in the practice of the present invention are shown by Williams, U.S. Pat. No. 4,273,712 and include, for example, tetrabutylammonium bromide, tetrapropylammonium bromide, tetrabutylammonium chloride, tetrabutylammonium fluoride, tetrabutylammonium acetate, tetrahexylammonium chloride, tetraheptylammonium chloride. Aliquat 336 phase transfer catalyst (methyltrioctylammonium chloride, manufactured by the General Mills Company), tetrabutylphosphonium bromide, tetrabutylphosphonium chloride, etc.

In the practice of the present invention, a nitro-N-organophthalimide-bisphenoxide salt mixture is prepared by adding a polychlorinated $C_{(1-3)}$ alkane solution of the nitro-N-organophthalimide to a mixture of the alkali metal bisphenoxide salt in a nonpolar organic solvent. Preferably, the addition of the polychlorinated $C_{(1-3)}$ alkane solution of the nitro-N-organophthalimide is added to the alkali metal bisphenoxide salt while the non-polar organic solvent is refluxing. This procedure has been found to remove the polychlorinated $C_{(1-3)}$ alkane from the reaction mixture along with water which is removed by azeotropic distillation. Those skilled in the art would know that non-polar organic solvents, defined more particularly below, are employed having a boiling temperature significantly above polychlorinated $C_{(1-3)}$ alkane.

A proportion of from about 1.9 to 2.1 moles of the nitrophthalimide, per mole of the alkali metal bisphenoxide salt is preferably used.

In preparing the nitro-N-organophthalimide, nitration of the N-organophthalimide can be achieved in accordance with the procedure of Cook et al, U.S. Pat. No. 4,005,102, assigned to the same assignee as the present invention, which is incorporated herein by reference. For example, the following procedure shows a typical method for preparing the nitro-N-organophthalimide in polychlorinated $C_{(1-3)}$ alkane:

A mixture of 16.1 grams (0.1 mol) of N-methylphthalimide dissolved in 30 cc. 98.3% sulfuric acid and 40 cc. methylene chloride was brought to a slow reflux. There was slowly added to the refluxing mixture 4.55 cc. (0.105 mol) 98.1% nitric acid over a period of 40 minutes. The mixture was stirred for an additional 1 hour at 41° C. while allowing some of the methylene chloride distilled. Thereafter, the temperature of the reaction mixture was raised to 90° C. for a period of 2 hours and the reaction mixture was allowed to cool. The mixture was diluted with 10 cc. of water and the mixture extracted with 200 cc. portions of methylene chloride. The methylene chloride extracts were combined and passed through a column of silica gel to remove traces of sulfuric acid.

In preparing the alkali metal bisphenoxide salts, the procedure shown by Williams et al, U.S. Pat. No. 4,257,953 and Williams, U.S. Pat. No. 4,273,712, both patents assigned to the same assignee as the present invention can be employed which also are incorporated herein by reference. Suitable organic solvents which can be employed in making the alkali metal bisphenoxide salts are, for example, hydrocarbon solvents and halogenated hydrocarbon solvents having a boiling point under atmospheric conditions in the range of from 80° C. to 180° C. Some of the solvents are, for example, toluene, xylene, octane, chlorobenzene, o-dichlorobenzene, etc.

A typical procedure for making the anhydrous bisphenoxide salt is shown in U.S. Pat. No. 4,259,953 is as follows:

A mixture of 364.8 parts of bisphenol-A, 254 parts of a 50.5% aqueous sodium hydroxide solution and 615 parts of water was refluxed under nitrogen for 0.5 hour to give a homogeneous solution. The mixture was cooled to 85° C. and about 1,030 parts of toluene was added. The mixture was heated at reflux for 4 hours and water was removed by azeotropic distillation.

Upon separation of the polychlorinated $C_{(1-3)}$ alkane from the nitro-N-organophthalimide-bisphenoxide alkali metal salt mixture, the nonpolar organic solvent used in the production of the bisphenoxide salt can be reduced in volume prior to the introduction of the phase transfer catalyst. The phase transfer catalyst can be added at a proportion of from 0.005 to 5 mole equivalent per mole equivalent of the alkali metal bisphenoxide salt, and preferably 0.02 to 0.04 mole equivalents of the phase transfer catalyst.

The resulting mixture can then be refluxed with agitation for 0.5 to 4 hours and thereafter diluted with additional organic solvent. The organic phase can then be extracted with aqueous alkali metal hydroxide and thereafter concentrated to produce the bis-etherphthalimide.

The bis-etherphthalimide also can be recovered from the reaction mixture by allowing the organic phase to cool followed by recovery of the bis-etherphthalimide by filtration. Another procedure can be used because of the partial solubility of the etherphalimide in various nonpolar organic solvents to precipitate the bis-etherphthalimide by use of a precipitating solvent, for example, methanol, followed by a standard recovery technique, such as filtration.

In order that those skilled in the art will be better able to practice the invention, the following examples are given by way of illustration and not by way of limitation. All parts are by weight.

EXAMPLE 1

A mixture of 15.00 g of bisphenol-A, 25 ml of water, 10.40 g of 50.62% sodium hydroxide and 250 ml of toluene was heated at reflux under azeotropic conditions until all the water had been removed. The anhydrous mixture was kept at reflux and 250 ml of methylene chloride containing 25.47 g of 4-nitro-N-methylphthalimide and 1.63 g of 3-nitro-N-methylphthalimide (a 94:6 ratio) was quickly added. The methylene chloride was recovered by flash distillation. At this point, 190 ml of toluene was removed by distillation and 0.80 g of the phase transfer catalyst, tetrabutylammonium bromide (0.038 eq.) was added. The mixture was heated at reflux for 1 hour, diluted with 50 ml of toluene and extracted with 120 ml of 1% NaOH solution for 15 minutes. The toluene solution was concentrated to give 32.9 g (91.6% yield) of bis-etherphthalimide Analysis of LC showed that the bis-etherphthalimide consisted of 91% by weight of 2,2-bis[4-(N-methylphthalimide-4-oxy)phenyl]propane, 6% of 2,2-bis[4-(N-methylphthalimide-3-oxy)phenyl]propane and about 3% of 2,2-[4-(N-methylphthalimide-4-oxy)phenyl][4-(N-methylphthalimide-3-oxy)phenyl]propane.

EXAMPLE 2

A solution of bisphenol-A dianion in toluene was prepared as described in Example 1. To this refluxing mixture was added 27.10 g of 4-nitro-N-methylphthalimide in 260 ml of methylene chloride. The methylene chloride was recovered by distillation through a short vigreaux column. At this point about 100 ml of toluene had been removed and 0.54 g of tetrabutylammonium bromide was added (0.025 eq.). The mixture was heated at reflux for 1 hour, cooled to 50° C., diluted with 200 ml of methanol and filtered to give 33.4 g (93% yield) of pure 2,2-bis[4-(N-methylphthalimide-4-oxy)phenyl]propane.

A mixture of anhydrous bisphenol-A dianion in toluene was prepared in accordance with Example 1. However, there was added to the mixture, 0.54 gram of tetrabutylammonium bromide, followed by the addition of 27.1 grams of 4-nitro-N-methylphthalimide in 250 ml of methylene chloride. The methylene chloride was removed by distillation through a short vigreaux column. After all the methylene chloride was removed, the reaction mixture was heated at reflux for 1 hour and cooled to 50° C. The mixture was then added to methanol resulting in a precipitate of product. The product was recovered by filtration. A 31% yield of product was obtained, which was found to be a mixture of 2,2-bis[4-(N-methylphthalimide-4-oxy)phenyl]propane and 4-nitro-N-methylphthalimide.

Based on the above results, those skilled in the art would known that the reduced yield of 2,2-bis[4-(N-methylphthalimide-4-oxy)phenyl]propane was based on the direct reaction of the bisphenol-A dianion and methylene chloride resulting in the production of unwanted polymeric by-products.

Although the above examples are directed to only a few of the very many variables which can be utilized in the practice of the method of the present invention, it should be understood that the method of the present invention involves the employment of a much broader variety of alkali metal salts of diphenoxides, nitro-N-organophthalimides and phase transfer catalysts which are shown in the description preceding these examples.

What we claim as new and desire to secure by Letters Patent of the United States is:

1. In the process for making bisetherphthalimide involving the steps of,
   (A) nitrating N-organophthalimide with concentrated nitric acid,
   (B) isolating the resulting nitro-N-organophthalimide from the nitration mixture of (A) as a solution in a polychlorinated $C_{(1-3)}$ alkane selected from methylene chloride, trichloroethane and 1,2-dichloroethane,
   (C) treating the polychlorinated $C_{(1-3)}$ alkane solution of (B), to remove traces of mineral acid,
   (D) evaporating the polychlorinated $C_{(1-3)}$ alkane from the solution of (C) to recover the nitro-N-organophthalimide,
   (E) reacting the nitro-N-organophthalimide of (D) with an alkali metal bisphenoxide salt,
the improvement which consists essentially of
   (1) adding the nitration mixture of (C) directly to a mixture of alkali metal bisphenoxide salt and a nonpolar organic solvent while the latter is refluxing, in amounts sufficient to produce a reaction mixture having about two moles of nitro-N-organophthalimide, per mole of bisphenoxide salt, which refluxing mixture of bisphenoxide salt and nonpolar organic solvent is obtained by heating under azeotropic conditions, a mixture of bisphenoxide, water, alkali metal hydroxide, and said nonpolar organic solvent until the mixture is substantially anhydrous,
   (2) distilling a major amount of the nonpolar organic solvent at temperatures of from 80° C. to 180° C. from the resulting mixture of (1), to provide for the complete removal of the polychlorinated $C_{(1-3)}$ alkane used in the treated solution of (C),
   (3) adding to the resulting mixture of (2), and effective amount of a phase transfer catalyst,
   (4) refluxing the resulting mixture of (3),
   (5) extracting the resulting mixture of (4) with aqueous alkali metal hydroxide and
   (6) effecting the removal of nonpolar organic solvent from the organic phase resulting from the extraction step of (5),
whereby the handling and isolation of the nitrophthalimide solids of (C), prior to the reaction of such solids with the alkali metal bisphenoxide salt of (E) is eliminated.

2. A process in accordance with claim 1, where the N-organophthalimide is N-methylphthalimide.

3. A process in accordance with claim 1, where the alkali metal bisphenoxide salt is the sodium salt of bisphenol-A.

4. A process in accordance with claim 1, where the phase transfer catalyst is tetrabutylammonium bromide.

5. A process in accordance with claim 1, where the organic solvent is toluene.

6. A method in accordance with claim 1, wherein the refluxing mixture of (4) is allowed to cool to effect the separation of bis-etherphthalimide from the nonpolar organic solvent.

7. A method in accordance with claim 1, where the mixture of (4) is combined with a precipitating organic solvent to effect the separation of the bis-etherphthalimide.

8. A process in accordance with claim 1, where the polychlorinated $C_{(1-3)}$ alkane is methylene chloride.

9. A process for making bis-etherphthalimide mixture of 2,2-bis[4-(N-methylphthalimide-4-oxy)phenyl]propane, 2,2-bis[4-(N-methylphthalimide-3-oxy)phenyl]propane, and 2,2-[4-(N-methylphthalimide-4-oxy)phenyl][4-(N-methylphthalimide-3-oxy)phenyl]propane which comprises
   (1) adding a methylene chloride solution of a mixture of 3-nitro-N-methylphthalimide and 4-nitro-N-methylphthalimide to a refluxing mixture of toluene and the disodium salt of bisphenol-A, obtained by refluxing toluene, bisphenol-A and a stoichiometric equivalent of sodium hydroxide until the water has been substantially removed by azeotropic distillation,
   (2) continuing to reflux the mixture of (1) until the methylene chloride has been separated by flash distillation,
   (3) effecting the removal of a major amount of toluene from the resulting mixture,
   (4) adding an effective amount of the phase transfer catalyst to the resulting mixture,
   (5) refluxing the resulting mixture followed by extracting the organic phase with an aqueous basic solution and
   (6) concentrating the resulting organic solvent phase to effect the recovery of a mixture of 2,2-bis[4-(N-methylphthalimide-3-oxy)phenyl]propane.

10. A method in accordance with claim 9, where there is utilized a methylene chloride solution of 4-nitro-N-methylphthalimide.

* * * * *